US00PP34460P2

(12) United States Plant Patent
Warner

(10) Patent No.: US PP34,460 P2
(45) Date of Patent: Aug. 2, 2022

(54) ***ROSA* PLANT NAMED 'CHEWAMBERNESS'**

(50) Latin Name: *Rosa hybrida*
Varietal Denomination: CHEWAMBERNESS

(71) Applicant: Spring Meadow Nursery, Inc., Grand Haven, MI (US)

(72) Inventor: Christopher Hugh Warner, Newport (GB)

(73) Assignee: Spring Meadow Nursery, Grand Haven, MI (US)

( * ) Notice: Subject to any disclaimer, the term of this patent is extended or adjusted under 35 U.S.C. 154(b) by 0 days.

(21) Appl. No.: 17/483,240

(22) Filed: Sep. 23, 2021

(51) Int. Cl.
*A01H 5/02* (2018.01)
*A01H 6/74* (2018.01)

(52) U.S. Cl.
USPC ..... Plt./111

(58) Field of Classification Search
USPC ..... Plt./101, 109, 111
See application file for complete search history.

*Primary Examiner* — Karen M Redden
(74) *Attorney, Agent, or Firm* — Cassandra Bright

(57) ABSTRACT

A new and distinct cultivar of *Rosa* plant named 'CHEWAMBERNESS' is disclosed, characterized by amber-yellow flowers, glossy foliage, and a self-climbing habit. Plants are healthy, vigorous, and free-flowering. The new variety is a *Rosa*, typically produced as an ornamental plant.

2 Drawing Sheets

Figure 1:
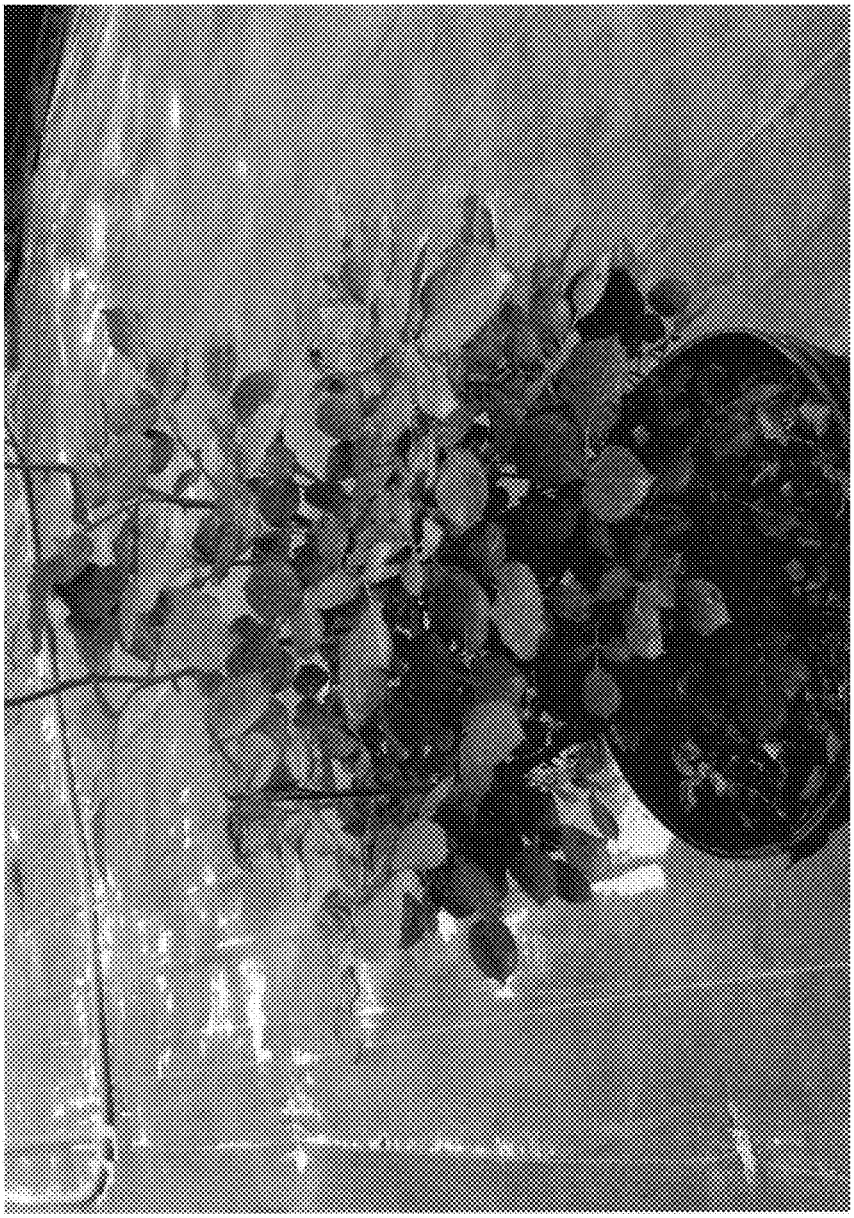

Latin name of the genus and species: *Rosa hybrida.*
Variety denomination: 'CHEWAMBERNESS'.

BACKGROUND OF THE INVENTION

The new *Rosa* cultivar is a product of a planned breeding program conducted by the inventor. The objective of the breeding program was to produce new, floriferous *Rosa* cultivars with good health, interesting colors, and self-climbing habits. The cross resulting in this new variety was made in June 2011, at a nursery in Brockton, UK.

The seed parent is the unpatented *Rosa* 'Gardener's Glory'. The pollen parent is the unpatented variety *Rosa* 'Tan04603'. The new variety was identified and selected as a potentially interesting selection in the Summer of 2013. Selection was made at the same nursery in Brockton, UK.

Asexual reproduction of the new cultivar 'CHEWAMBERNESS' was first performed in August 2013 in Brockton, UK, by softwood cuttings. Subsequent propagation has shown that the unique features of this cultivar are stable and reproduced true to type in successive generations.

SUMMARY OF THE INVENTION

The cultivar 'CHEWAMBERNESS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CHEWAMBERNESS'. These characteristics in combination distinguish 'CHEWAMBERNESS' as a new and distinct *Rosa* cultivar:

1. Free-flowering.
2. Glossy foliage.
3. Excellent health.
4. Attractive amber-yellow flower color.
5. Self-climbing growth habit.

PARENT COMPARISONS

Plants of the new cultivar 'CHEWAMBERNESS' are similar to the seed parent in most horticultural characteristics. However, characteristics of the new cultivar differ in the following:

1. The new variety has amber-yellow flowers, while the seed parent has yellow flowers.
2. The new variety has a self-climbing habit, while the seed parent has a climbing habit.

Plants of the new cultivar 'CHEWAMBERNESS' are similar to the pollen parent in most horticultural characteristics. However, characteristics of the new cultivar differ in the following:

1. The new variety is a more vigorous plant than the pollen parent.
2. The new variety has amber-yellow flowers, while the pollen parent has peachy-yellow flowers.
3. The new variety has medium-sized flowers, while the pollen parent has larger flowers.

COMMERCIAL COMPARISON

Plants of 'CHEWAMBERNESS' are similar in some horticultural characteristics to the variety *Rosa* 'CHEWGEWEST', U.S. Plant Pat. No. 31,005. The new variety, however, differs in the following:

1. Flowers of 'CHEWAMBERNESS' are amber-yellow with less color variation, while flowers of 'CHEWGEWEST' are yellow-orange, turning slightly pink near tips/margins.
2. Plants of 'CHEWAMBERNESS' have a climbing habit, while 'CHEWGEWEST' has a shrub-like habit.
3. Flowers of 'CHEWAMBERNESS' have more petals and petaloids than flowers of 'CHEWGEWEST'.

4. 'CHEWAMBERNESS' has single to multiple terminal flowers per lateral stem, while 'CHEWGEWST' typically has a single terminal flower per lateral stem.

BRIEF DESCRIPTION OF THE PHOTOGRAPHS

The accompanying photograph in FIG. 1 illustrates in full color a typical plant of 'CHEWAMBERNESS' grown in a poly-greenhouse at a commercial nursery in Grand Haven, Mich. This plant is approximately 2 years old, shown in a 2 gallon pot.

Figure 2:
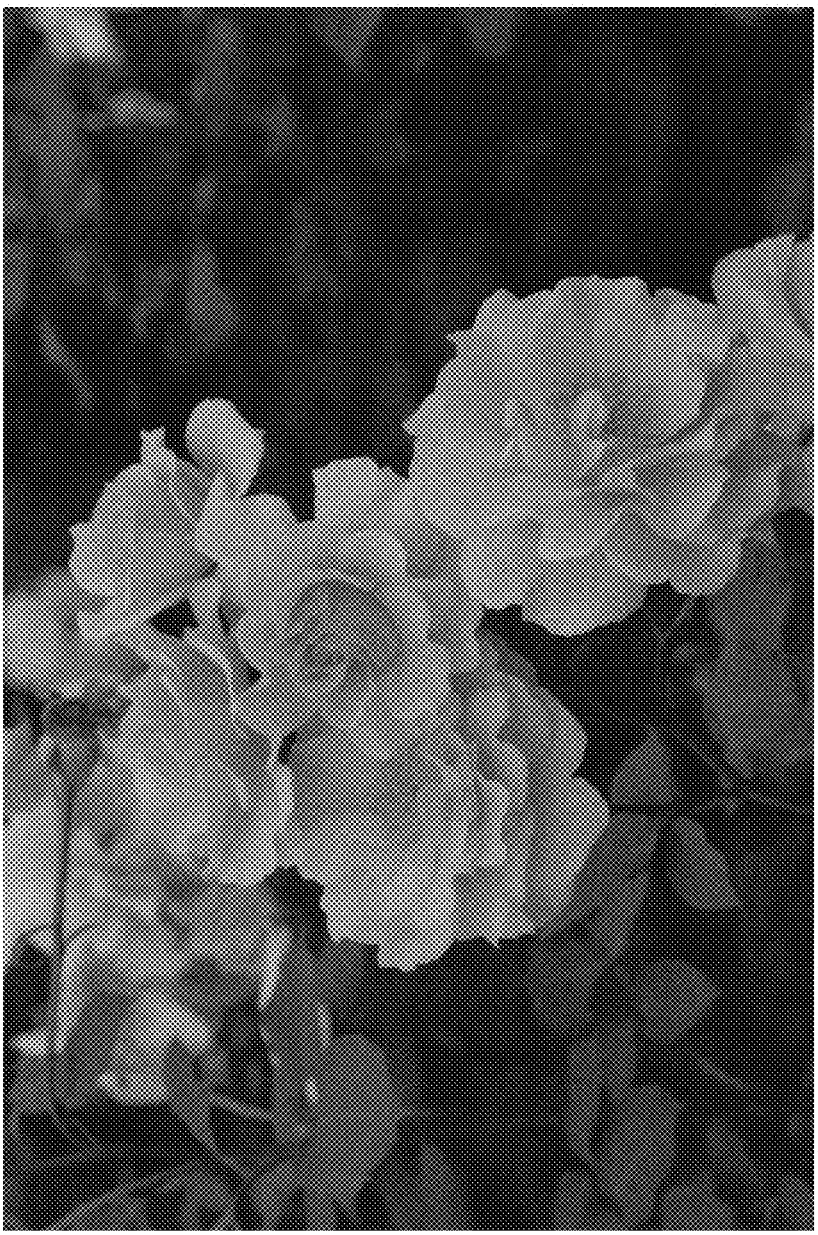

FIG. 2 illustrates a closer view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'CHEWAMBERNESS' plant. This plant was grown in a poly-greenhouse in a 3 gallon container, in Grand Haven, Mich. The plant described is approximately 2-3 years old. Temperatures ranged from 5-10° C. at night and 18° C. to 27° C. during the day. No artificial light, photoperiodic treatments were given to the plants. Measurements and numerical values represent averages of typical plant types.

Botanical classification: *Rosa hybrida* 'CHEWAMBERNESS'.

Market Category: Climbing garden rose.

PROPAGATION

Time to initiate roots: 30 days at approximately 20° C.

Time to produce a rooted plant: 120 days.

Root description: Fleshy and fibrous, moderate branching, medium root thickness. White in color, not effectively measured with a color chart.

PLANT

Plant type: Perennial.

Age of plant described: Approximately 2 to 3 years old.

Growth habit: Upright, self-climbing.

Height: 60 cm.

Plant spread: 55 cm.

Growth rate: Moderate.

Plant vigor: Good.

Branching characteristics: Basal branching, pinching required.

Length of lateral branches: 45 cm.

Diameter of lateral branches: 4 mm.

Quantity of lateral branches: 10 to 15.

Internode length: 4 cm.

Stem:

*Appearance/shape.*—Round/thorny.

*Aspect.*—Very upright.

*Strength.*—Strong.

*Color.*—Near RHS Green 143C, with tinges of Greyed-Red 180B on topmost portions of stems.

*Pubescence.*—None.

Thorns:

*Number per linear centimeter.*—2 to 3.

*Shape.*—Narrow, bent downward.

*Apex.*—Acicular.

*Base.*—Obtuse.

*Length.*—6 mm.

*Width.*—4 mm at base, about 2 mm at apex.

*Color, immature.*—RHS Greyed-Red 180D on top side, fading to Yellow-Green 145B on under side.

*Color, mature.*—RHS Greyed-Red 180D on top side, fading to Yellow-Green 145B on under side.

FOLIAGE

Leaf:

*Arrangement.*—Alternate.

*Quantity.*—10.

*Average length.*—8 cm.

*Average width.*—7 cm.

*Pubescence.*—None.

Leaflet:

*Quantity.*—3 to 5 per leaf.

*Terminal length.*—4.5 cm.

*Terminal width.*—3 cm.

*Lateral length.*—4 cm.

*Lateral width.*—3 cm.

*Shape.*—Elliptic.

*Apex.*—Acuminate.

*Base.*—Obtuse.

*Texture.*—Smooth, coriaceous.

*Margin.*—Serrulate.

*Color.*—Young, Upper side: RHS Green 137A. Young, Under side: RHS Yellow-Green 147B. Mature, Upper side: RHS Green 137A. Mature, Under side: RHS Yellow-Green 147B.

*Venation.*—Type: Pinnate. Venation Color, Upper side: RHS Yellow-Green 145A, with tinges of Greyed-Red 180D. Venation Color, Under side: RHS Yellow-Green 145A, with tinges of Greyed-Red 180D.

Petiole:

*Leaf.*—Length: 3 cm. Diameter: 2 mm. Color: Upper Surface: RHS Yellow-Green 145A, with tinges of Greyed-Red 180D. Lower Surface: RHS Yellow-Green 145A. Texture: Smooth and glossy, both surfaces.

*Leaflet.*—Length: 1 mm. Diameter: 1 mm. Color: Upper Surface: RHS Yellow-Green 145A, with tinges of Greyed-Red 180D. Lower Surface: RHS Yellow-Green 145A. Texture: Smooth and glossy, both surfaces.

Stipule:

*Quantity.*—2.

*Shape.*—Linear/acicular.

*Apex.*—Acicular.

*Base.*—Fused along petiole.

*Margin.*—Entire.

*Length.*—15 mm.

*Width.*—2 mm.

*Texture.*—Smooth, both surfaces.

*Color.*—Upper Surface: RHS Yellow-Green 145A. Lower Surface: RHS Yellow-Green 145A.

Foliage durability to stress: Good.

FLOWER

Natural flowering season: Spring through Summer.

Flower:

*Arrangement.*—1 to 6 blooms arranged terminally on lateral branches.

*Form.*—Double, whorled.

*Shape.*—Round whorl.

*Persistent or self-cleaning.*—Self-cleaning.

*Fragrance.*—Light, sweet, citrusy.

*Aspect.*—Upright.

*Diameter.*—9 cm.

*Depth.*—4 cm.

Bud:

*Shape.*—Ovate.

*Length.*—2 cm.

*Diameter.*—2 cm.

*Color.*—RHS Green 138A.

Petals:

*Quantity.*—About 20.

*Appearance.*—Vibrant, recurve, rounded, with curling margins.

*Arrangement.*—Double whorl.

*Length.*—External Whorl: 4.5 cm. Internal Whorl: 3.5 cm.

*Width.*—External Whorl: 5 cm. Internal Whorl: 3 cm.

*Shape.*—External Whorl: Orbicular. Internal Whorl: Obovate.

*Apex.*—Retuse.

*Base.*—Unfused.

*Margin.*—Slightly crenate.

*Texture.*—Smooth and silky.

*Color.*—When Opening, Upper Surface: RHS Greyed-Orange N163B, with Yellow 8A near base. When Opening, Lower Surface: RHS Greyed-Orange N172C, with Yellow 8A near base. Fully Opened, Upper Surface: RHS Greyed-Yellow 162A. Fully Opened, Lower Surface: RHS Greyed-Orange 165C. At Petal Drop, Upper Surface: RHS Red 36D flushed Yellow 12D. At Petal Drop Lower Surface: RHS Red 36D flushed Yellow-Orange 20D.

Petaloids:

*Appearance.*—Irregular, curved.

*Arrangement.*—Whorled.

*Quantity.*—4 to 6.

*Shape.*—Irregular.

*Margin.*—Slightly crenate.

*Length.*—1 to 2 cm.

*Width.*—0.5 to 1 cm.

*Color.*—Immature: RHS Greyed-Orange 163C. Mature: RHS Orange 26B.

Sepals:

*Appearance.*—Rough, recurved toward stem.

*Arrangement.*—Whorl around base.

*Quantity.*—5.

*Length.*—2.5 cm.

*Width.*—1 cm.

*Shape.*—Triangular.

*Margin.*—Entire.

*Apex.*—Acuminate.

*Base.*—Fused.

*Color.*—Immature, Upper Side: RHS Green 143B, with White 155A pubescence. Immature, Under Side: RHS Green 143B. Mature, Upper Side: RHS Green 143B, with White 155A pubescence. Mature, Under Side: RHS Green 143B.

*Texture.*—Upper surface: Softly pubescent. Lower surface: Rough, some coarse pubescence.

Calyx:

*Shape.*—Collar-like with recurved sepals arranged in a whorl.

*Length.*—2 cm.

*Width.*—1 cm.

Peduncles:

*Length.*—4 cm.

*Diameter.*—3 mm.

*Angle.*—Upright, 75-90°.

*Strength.*—Strong.

*Texture.*—Slightly prickly.

*Color.*—Near RHS Green 143C, with some fading to Greyed-Red 180B with sun exposure.

Pedicels: None.

REPRODUCTIVE ORGANS

Stamens:

*Number.*—About 130.

*Filament length.*—About 12 mm.

*Filament color.*—RHS Greyed-Yellow 162A.

Anthers:

*Shape.*—Club-like, dorsifixed.

*Length.*—3 mm.

*Color.*—RHS Greyed-Yellow 162A.

*Pollen color.*—RHS Greyed-Yellow 162A.

*Pollen amount.*—Moderate.

Pistil:

*Number.*—70.

*Length.*—10 mm.

*Style.*—Length: 9 mm. Color: RHS Greyed-Yellow 162A.

*Stigma.*—Shape: Rounded. Color: RHS Greyed-Yellow 162A.

*Receptacle.*—Height: 1 cm. Diameter: 1 cm. Shape: Orbicular. Texture: Smooth. Color: RHS Green 143B.

OTHER CHARACTERISTICS

Seeds: Not observed.

Disease/pest resistance: Above average disease resistance to black spot (*Diplocarpon rosae*) and powdery mildew (*Sphaerotheca pannosa* var. *rosae*), typically found on garden roses. Average tolerance for typical garden rose pests.

Temperature tolerance: Low temperature tolerance to −31° C., high temperature tolerance to at least 38° C.

What is claimed is:

1. A new and distinct cultivar of *Rosa* plant named 'CHEWAMBERNESS' as herein illustrated and described.

* * * * *